United States Patent [19]
Rupp et al.

[11] Patent Number: 5,762,636
[45] Date of Patent: Jun. 9, 1998

[54] INTRAVASCULAR CATHETER

[75] Inventors: Mark E. Rupp; Joseph S. Ulphani, both of Omaha, Nebr.

[73] Assignee: Board of Regents - Univ of Nebraska, Lincoln, Nebr.

[21] Appl. No.: 822,882

[22] Filed: Mar. 24, 1997

[51] Int. Cl.⁶ .................................................. A61M 5/00
[52] U.S. Cl. ................................. 604/264; 604/175
[58] Field of Search ............................ 604/164, 174, 604/175, 264, 280; 128/DIG. 26; 606/232, 233

[56] References Cited

U.S. PATENT DOCUMENTS 4,366,817  1/1983  Thomas .................................. 604/174
4,840,613  6/1989  Balbierz ................................... 604/51

*Primary Examiner*—Mark Bockelman
*Assistant Examiner*—Deborah Blyveis
*Attorney, Agent, or Firm*—Zarley, McKee, Thomte, Voorhees & Sease; Mark D. Frederiksen

[57] ABSTRACT

A catheter includes an inner cannula formed of a soft flexible stretchable biocompatible material and attached to a needle on a hub at the proximal end thereof. The inner cannula is slidably journaled through an outer cannula formed of the same biocompatible material, the inner cannula projecting outwardly out of the distal end of the outer cannula. The outer cannula proximal end is connected to the hub by a tube of heat shrinkable material. Three collars are mounted on the projecting portion of the inner cannula, the distal collar clamped in position to prevent slidable movement of the intermediate and proximal collars off of inner cannula, and the intermediate and proximal collars slidably mounted on the inner cannula.

17 Claims, 2 Drawing Sheets

INTRAVASCULAR CATHETER

TECHNICAL FIELD

The present invention relates generally to intravascular catheters for laboratory animals, and more particularly to an improved intravascular catheter which permits repeated drug administration or multiple blood samplings of conscious unrestrained rats.

BACKGROUND OF THE INVENTION

While intravascular catheters for rodents are generally known in the prior art, they suffer several problems. First, movement of the rodent about the cage can easily pull the catheter free of the sutures securing the catheter in the vessel.

Prior art permanent catheters must be tethered to the rodent's cage in order to prevent the rodent from biting or chewing on the catheter. Such tethering typically requires a swivel joint to permit rotation of the catheter at its connection to the cage, thereby dramatically increasing the cost.

Continuous movement and manipulation of the catheter about the swivel can cause intraluminal damage to the catheter, requiring repair or replacement.

Other problems with prior art catheters result from the common use of polyethylene tubing, or combinations of polyethylene and other materials, which are deficient in long term biocompatability. In addition, a single catheter tube is subject to sharing forces, damage from biting or other contact with the animal, and other damage from direct exposure.

SUMMARY OF THE INVENTION

It is therefore a general object of the present invention to provide an improved intravascular catheter for rats and other rodents.

Another object is to provide an improved intravascular catheter which permits stretching and other movement of the catheter within the body of the rodent without stressing the sutures retaining the catheter in position in the vessel.

A further object of the present invention is to provide an improved intravascular catheter with improved stability and durability at the connection of the catheter to its hub.

Yet another object is to provide an improved catheter having inner and outer cannulas, the outer cannula protecting the inner cannula from damage.

Yet a further object of the present invention is to provide an improved intravascular catheter which can be adapted to prior art tether systems or other restraint systems.

Still another object is to provide an improved intravascular catheter which is economical to manufacture and simple to use.

These and other objects of the present invention will be apparent to those skilled in the art.

The catheter of the present invention includes an inner cannula formed of a soft flexible stretchable biocompatible material and attached to a needle on a hub at the proximal end thereof. The inner cannula is slidably journaled through an outer cannula formed of the same biocompatible material, the inner cannula projecting outwardly out of the distal end of the outer cannula. The outer cannula proximal end is connected to the hub by a tube of heat shrinkable material. Three collars are mounted on the projecting portion of the inner cannula, the distal collar clamped in position to prevent slidable movement of the intermediate and proximal collars off of inner cannula, and the intermediate and proximal collars slidably mounted on the inner cannula.

DESCRIPTION OF THE PREFERRED EMBODIMENT

Figure 1:
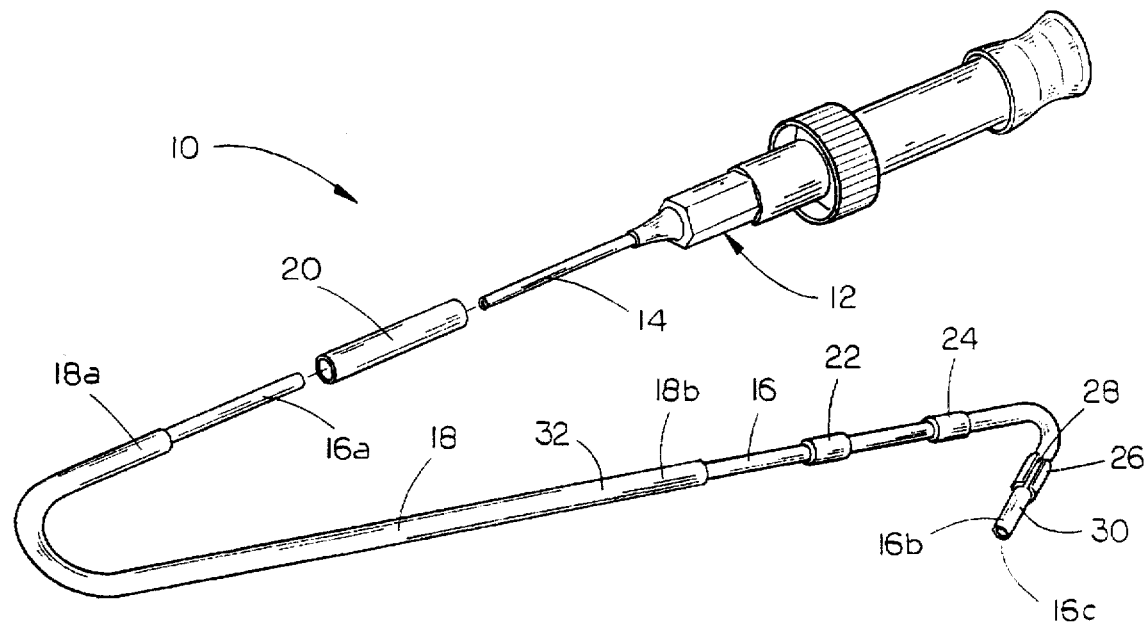
FIG. 1 is an enlarged perspective view of the catheter of the present invention with the hub shown exploded from the upper end of the remainder of the catheter.

Referring now to the drawings, in which similar or corresponding parts are identified with the same reference numeral and more particularly to FIG. 1, the catheter of the present invention is designated generally at 10 and includes a rigid hub 12 with a needle 14 projecting from a distal end thereof, and a flexible, stretchable cannula 16 mounted on the needle 14.

Figure 3:
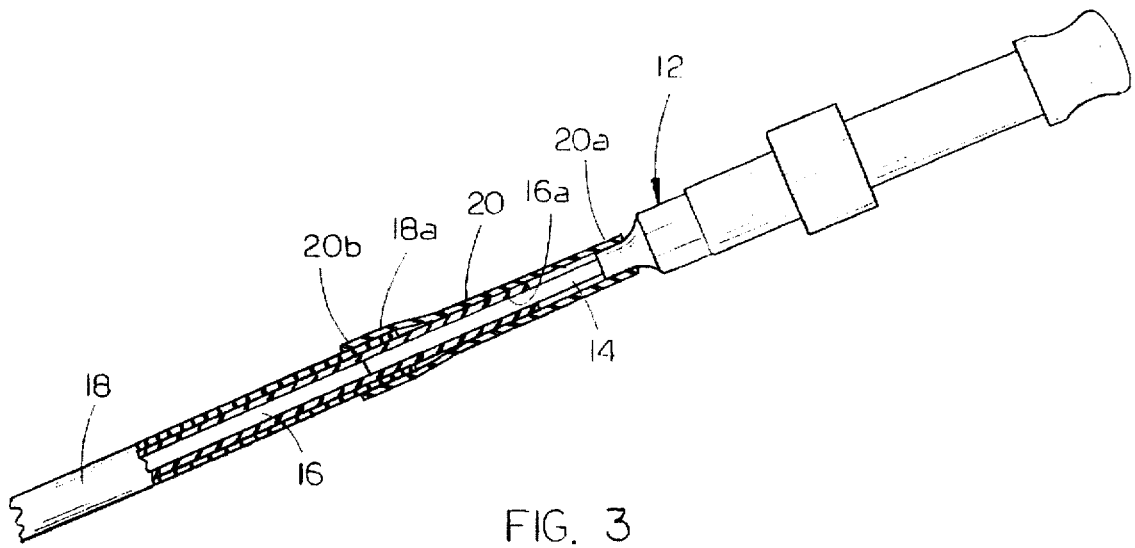
FIG. 3 is an enlarged view of the hub end of the catheter with portions thereof shown in section.

Cannula 16 has proximal and distal ends 16a and 16b respectively, and is formed of a soft biocompatible medical grade silicone rubber such as that manufactured under the brand name Silastic®, permitting great flexibility and stretchability of the cannula. Cannula 16 has an inner diameter which permits proximal end 16a to slide over the distal end of needle 14 for attachment to the hub 12, as shown in FIG. 3. A second cannula 18 has a length shorter than that of first cannula 16 and an inner diameter greater than the outer diameter of first cannula 16 to permit cannula 16 to be slidably journaled within the outer second cannula 18. Outer cannula 18 is also formed of a soft biocompatible medical grade silicone rubber which is both flexible and stretchable. The proximal end 18a of outer cannula 18 is positioned so as to overlap the distal end of needle 14, as shown in FIG. 3. A short tube 20 formed of a heat shrinkable material has a length greater than the length of needle 14, with a proximal end 20a overlapping a distal end of hub 12, and a distal end 20b overlapping the proximal end of outer cannula 18, and extending beyond the length of needle 14. The application of heat to tube 20 causes the tube to shrink and connect inner and outer cannulas 16 and 18 to needle 14. Tube 20 is preferably formed of a stiff material so as to stabilize the juncture of cannulas 16 and 18 with needle 14, and prevent sharp bending of cannulas 16 and 18 at the distal end of needle 14.

Referring once again to FIG. 1, it can be seen that the distal end 16b of inner cannula 16 extends beyond the distal end 18b of outer cannula 18. Three collars 22, 24, and 26 are provided on this portion of inner cannula 16 which projects out the distal end of outer cannula 18. Collars 22, 24, and 26 are formed of the same biocompatible resilient and stretchable material as cannulas 16 and 18. The proximal collar 22 and intermediate collar 24 preferably have diameters similar to that of outer cannula 18 to permit free sliding along inner cannula 16.

Distal collar 26 has an inner diameter smaller than the outer diameter of inner cannula 16. A longitudinal cut 28 along the length of collar 26 permits the distal collar to be opened to receive inner cannula 16 therein. The diameter of collar 26 thereby causes the collar to "clamp" onto cannula 16 and grip the cannula to prevent slidable movement of distal collar 26 along cannula 16. Thus, while distal collar 26 may be easily positioned on the distal end of inner cannula 16, it will remain clamped in position on cannula 16 once placed.

A mark 30 is imprinted in permanent or indelible ink or the like on the distal end 16b of inner cannula 16, spaced from the distal tip 16c a distance to indicate the optimal insertion point of inner cannula 16 into the vein. A similar mark 32 may be imprinted on outer cannula 18 to indicate the optimal insertion point of the outer cannula into the body of the animal.

Figure 4:
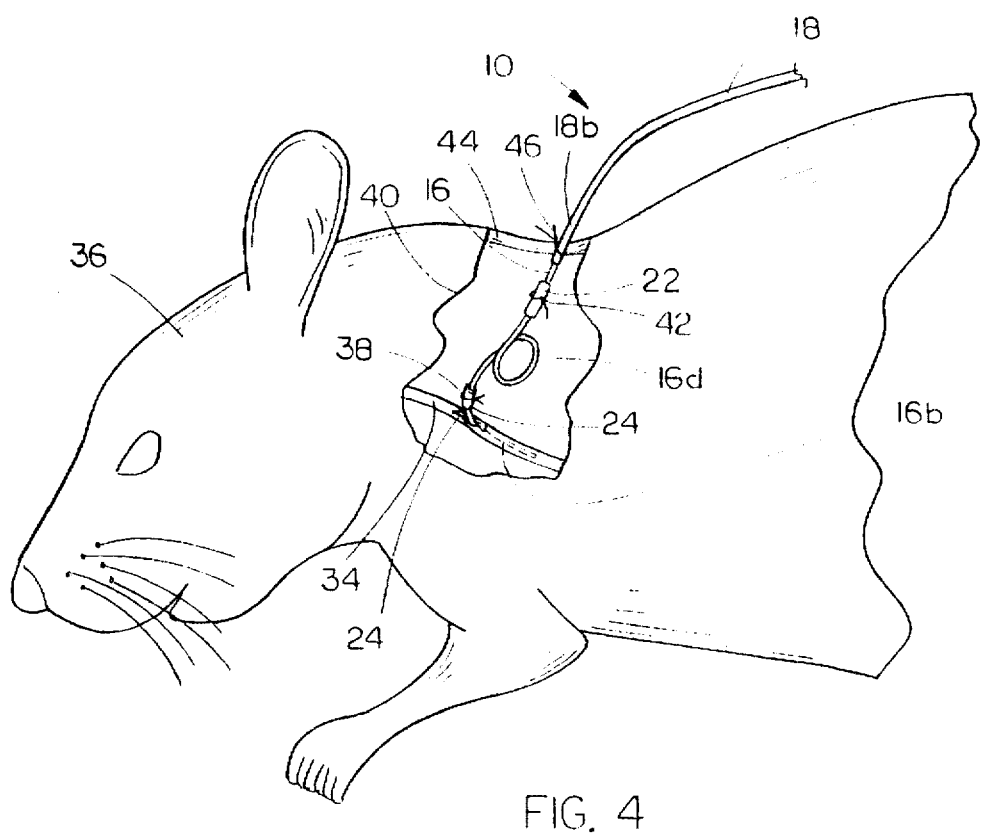
FIG. 4 is an enlarged elevational view of the attachment of the catheter to a rat, with portions broken away to show detail.

Referring now to FIG. 4, catheter 10 is shown in use inserted within vessel 34 (in this case the jugular vein) of a rat 36. Distal collar 26 serves to retain proximal and intermediate collars 22 and 24 on inner cannula 16 during preparation time, until the time of insertion. Distal collar 26 is then removed before implanting the catheter. Intermediate collar 24 is positioned on inner cannula 16 at a predetermined distance from the distal tip, so as to position intermediate collar 24 adjacent vessel 34. A suture 38 affixes intermediate collar 24 in position adjacent vessel 34.

Proximal collar 22 slides along cannula 16 away from intermediate collar 24, to permit the formation of a loop 16d between collars 22 and 24. Proximal collar 22 is then attached to subcutaneous tissue 40 with a suture 42. The distal end 18b of outer cannula 18 is then affixed in position inserted through the skin 44 of rat 36, with a suture 46.

It can be seen that intermediate collar 24 permits suture 38 to be tightened to securely affix inner cannula 16 in position, while preventing suture 38 from damaging cannula 16 or restricting flow of fluid therethrough. Similarly, proximal collar 22 is securely fastened to the subcutaneous tissue 40 by suture 42, yet permits inner cannula 16 to stretch and slide therethrough. Loop 16d is utilized to permit lengthening and other movement of cannula 16 within rat 36, as the rat moves about. Loop 16d also assists in preventing the application of any tension which might otherwise dislodge cannula 16 from vessel 34.

Figure 2:
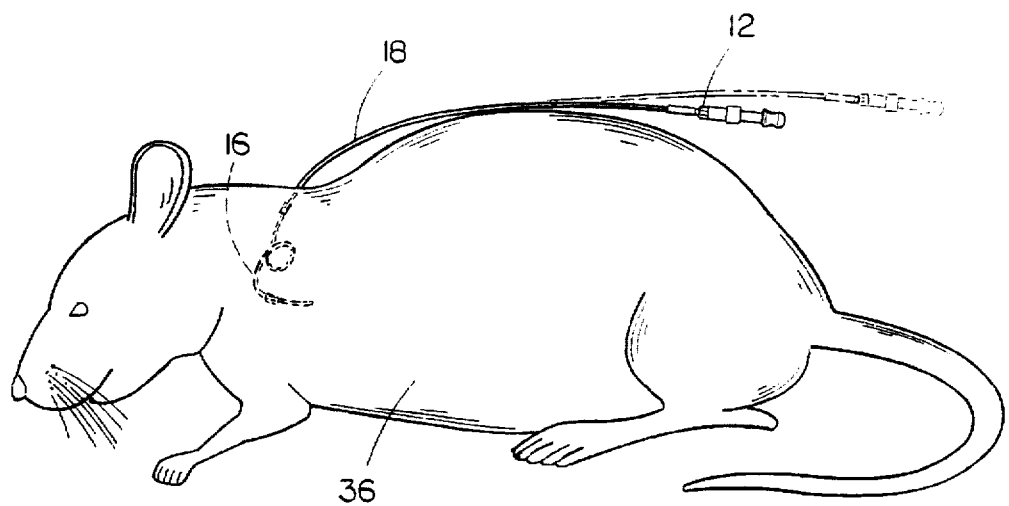
FIG. 2 is an elevational view of the catheter attached to a rat.

The securement of outer cannula 18 to the skin 44 of rat 36 permits movement of inner cannula 16 without regard to tugs or pulls on outer cannula 18 by virtue of movement of the rat 36 about its cage. As shown in FIG. 2, stretching of outer cannula 18 by virtue of pulling on hub 12 will not affect the connection of inner cannula 16 within rat 36.

Whereas the intravascular catheter of the present invention has been shown and described in connection with the preferred embodiment thereof, many modifications, substitutions and additions may be made which are within the intended broad scope of the appended claims.

We claim:

1. A catheter, comprising:

an inner cannula having proximal and distal ends, formed of a flexible, stretchable, biocompatible material;

a hub having a needle projecting therefrom, said needle having a projecting distal end;

said inner cannula proximal end connected to the needle with the inner cannula distal end projecting beyond the distal end of the needle, for transmission of fluid from the needle therethrough; and said inner cannula slidably journaled through an outer cannula formed of a flexible, stretchable biocompatible material, the inner cannula having a length greater than that of the outer cannula such that the inner cannula includes a distal portion projecting from a distal end of the outer cannula;

said outer cannula having a proximal end connected to said hub and a length greater than the length of the needle.

2. The catheter of claim 1, wherein the outer cannula proximal end extends to a position between the proximal and distal ends of the needle, and further comprising a tube having a distal end mounted to the proximal end of the outer cannula and a proximal end mounted to the hub, said tube mounting the outer cannula to the hub to prevent separation of the hub from the outer cannula.

3. The catheter of claim 2, wherein said tube has a length extending distally beyond the distal end of the needle and is formed of a stiff material such that the inner and outer cannulas will flex at the distal end of the tube, beyond the distal end of the needle.

4. A catheter, comprising:

an inner cannula having proximal and distal ends, formed of a flexible, stretchable, biocompatible material;

a hub having a needle projecting therefrom, said inner cannula proximal end connected to the needle for transmission of fluid therethrough; and said inner cannula slidably journaled through an outer cannula formed of a flexible, stretchable biocompatible material, the inner cannula having a length greater than that of the outer cannula such that the inner cannula includes a distal portion protecting a from a distal end of the outer cannula;

said outer cannula having a proximal end connected to said hub and extending over a distal end of the needle, a tube having a distal end mounted to the proximal end of the outer cannula and a proximal end mounted to the hub, said tube connecting the outer cannula to the hub;

said tube being formed of a stiff heat-shrink material and mounted to the hub and outer cannula by heat-shrinking, said tube having a length extending distally beyond the distal end of the needle.

5. The catheter of claim 4, further comprising a distal collar detachably mounted on the distal portion of the inner cannula for non-slidable connection on the cannula.

6. The catheter of claim 5, wherein said distal collar is formed of a resilient, flexible material having memory and has an inner diameter less than an outer diameter of the inner cannula, and further including a longitudinal cut through one wall of the collar extending the entire length thereof, said collar detachably clamped in position on the inner cannula by the memory of the material.

7. The catheter of claim 6, further comprising a proximal collar slidably mounted on the distal portion of the inner cannula, between the distal collar and outer cannula distal end, said proximal collar formed of a biocompatible material.

8. The catheter of claim 7, further comprising an intermediate collar slidably mounted on a distal portion of the inner cannula, between the distal and proximal collars, said intermediate collar formed of a biocompatible material.

9. The catheter of claim 8, wherein said proximal and intermediate collars are formed of flexible, stretchable material.

10. The catheter of claim 5, further comprising a proximal collar slidably mounted on the distal portion of the inner cannula, between the distal collar and outer cannula distal end, said proximal collar formed of a biocompatible material.

11. The catheter of claim 10, further comprising an intermediate collar slidably mounted on a distal portion of the inner cannula, between the distal and proximal collars, said intermediate collar formed of a biocompatible material.

12. The catheter of claim 11, wherein said proximal and intermediate collars are formed of flexible, stretchable material.

13. A catheter, comprising:

an inner cannula having proximal and distal ends, formed of a flexible, stretchable, biocompatible material;

a hub having a needle projecting therefrom, said inner cannula proximal end connected to the needle for transmission of fluid therethrough;

said inner cannula slidably journaled through ah an outer cannula formed of a flexible, stretchable biocompatible material, the inner cannula having a length greater than that of the outer cannula such that the inner cannula includes a distalportion projecting from a distal end of the outer cannula;

said outer cannula having a proximal end connected to said hub; and a distal collar detachably mounted on the distal portion of the inner cannula for non-slidable connection on the cannula.

14. The catheter of claim 13, wherein said distal collar is formed of a resilient, flexible material having memory and has an inner diameter less than an outer diameter of the inner cannula, and further including a longitudinal cut through one wall of the collar extending the entire length thereof, said collar detachably clamped in position on the inner cannula by the memory of the material.

15. The catheter of claim 14, further comprising a proximal collar slidably mounted on the distal portion of the inner cannula, between the distal collar and outer cannula distal end, said proximal collar formed of a biocompatible material.

16. The catheter of claim 15, further comprising an intermediate collar slidably mounted on a distal portion of the inner cannula, between the distal and proximal collars, said intermediate collar formed of a biocompatible material.

17. The catheter of claim 16, wherein said proximal and intermediate collars are formed of flexible, stretchable material.

* * * * *